United States Patent [19]

Matoba et al.

[11] Patent Number: 5,464,612
[45] Date of Patent: Nov. 7, 1995

[54] SOLID PREPARATION COMPRISING ION EXCHANGER AND ACTIVE AGENT

[75] Inventors: Hiroshi Matoba, Osaka; Shinji Ohmori, Ikeda; Hiroyoshi Koyama, Mishima; Toshio Kashihara, Suita, all of Japan

[73] Assignee: Takeda Chemical Industries, Ltd., Osaka, Japan

[21] Appl. No.: 233,964

[22] Filed: Apr. 28, 1994

[30] Foreign Application Priority Data

Apr. 28, 1993 [JP] Japan ................... 5-125091

[51] Int. Cl.$^6$ ................................. A61K 31/74
[52] U.S. Cl. ................. 424/78.1; 424/78.16; 424/78.11; 514/974
[58] Field of Search ................... 424/482, 483, 424/78.1, 78.16, 78.11

[56] References Cited

U.S. PATENT DOCUMENTS

| | | | |
|---|---|---|---|
| 3,954,470 | 7/1971 | Borodkin | 424/483 |
| 4,221,778 | 9/1980 | Raghunathan | 424/483 |
| 4,762,709 | 8/1988 | Sheumaker | 424/483 |
| 4,996,047 | 2/1991 | Kelleher et al. | 424/483 |

FOREIGN PATENT DOCUMENTS

| | | |
|---|---|---|
| 0212641 | 3/1987 | European Pat. Off. . |
| 0418588 | 3/1991 | European Pat. Off. . |
| 2676364 | 11/1992 | France . |
| 383552 | 10/1964 | Switzerland . |
| 856501 | 12/1960 | United Kingdom . |
| 1462356 | 1/1977 | United Kingdom . |
| 2176999 | 1/1987 | United Kingdom . |
| WO88/03795 | 6/1988 | WIPO . |

OTHER PUBLICATIONS

Research Disclosure 17619 Derwent WPI Acc. No. 78–92367 A/51.
Research Disclosure 17620 Derwent WPI Acc. No. 78–92368A/51.

*Primary Examiner*—Thurman K. Page
*Assistant Examiner*—Peter Kulkosky
*Attorney, Agent, or Firm*—Wenderoth, Lind & Ponack

[57] ABSTRACT

(A) A clad powdery or granular preparation of a medicinally active ingredient and (B) a powdery or granular ion exchanger such as a cation exchange resin are blended to prepare a solid preparation. The active ingredient includes β-lactam antibiotics having a basic group. The clad powdery or granular preparation includes not only coated preparation wherein the active ingredient or preparation is coated but also a variety of preparations in which the contact of the active ingredient with the ion exchanger is suppressed or inhibited. Polymers such as a water-soluble polymer, an enteric polymer and so on can be used as the coating agent for the coated preparation. The using amount of the ion exchanger is about 10 to 5,000 parts by weight per 100 parts by weight of the active ingredient. Said solid preparation can remarkably decrease the unpleasant taste and odor of the active ingredient such as bitterness, being excellent in dissolution property and absorbability of the active ingredient.

30 Claims, No Drawings

SOLID PREPARATION COMPRISING ION EXCHANGER AND ACTIVE AGENT

FIELD OF THE INVENTION

This invention relates to a solid preparation providing for improved compliance through the masking of the unpleasant taste and/or odor of a drug and a method of producing the same. The invention finds application in the field of medicines.

BACKGROUND OF THE INVENTION

Many medicinally active ingredients have unpleasant tastes, e.g. bitter or pungent tastes, and/or unpleasant odors. Because such medicinal substances cannot be easily taken orally by young children and the aged, the dosage and administration recommendations are sometimes neglected so that the so-called compliance problem occurs at times.

Therefore, to provide pharmaceutical preparations with improved tastes and odors, several approaches have heretofore been suggested. Among them are (1) the method comprising adding a corrigent such as a sweetener to a medicinally active ingredient and processing the mixture into a preparation, (2) the method in which the medicinally active ingredient is absorbed physically on a carrier, (3) the masking method comprising microencapsulating or cladding the medicinally active ingredient with a wall-forming or coating material, and (4) the method comprising complexing the medicinally active ingredient with an ion exchange resin.

The first-mentioned method (1), however, has the disadvantage that depending on the threshold bitterness of the medicinally active ingredient, inter-patient differences in gustatory sensibility, etc., the bitterness, for instance, cannot be sufficiently controlled. The second-mentioned method (2) calls for the use of an absorbent in a large quantity for effective absorption of the medicinally active ingredient, leading to an increase in dosage unit size. The third-mentioned method (3) is also disadvantageous in that an excessive increase in wall or film thickness detracts from the gastrointestinal absorption of the medicinally active ingredient while an excessive reduction in wall or film thickness results in a premature development of bitterness, with the result that its bitterness can hardly be controlled efficiently without decreasing the absorbability of the active ingredient. Moreover, the pharmaceutical manufacturing process is complicated of necessity and, yet, no commensurate suppression of the unpleasant taste and/or odors can be expected.

Regarding the fourth-mentioned method (4), British Patent 1462356, Research Disclosure 176019 (Derwent WPI Acc No. 78-92367A/51) and Research Disclosure 176020 (Derwent WPI Acc No. 78-92368A/51) describe complexes of β-lactam antibiotics with cation exchange resins and complexes of penicillin drugs with anion exchange resins. By this technology employing an ion exchange resin, the bitterness of medicinally active ingredients can be fairly well controlled.

However, it takes a large quantity of an ion exchange resin, relative to a drug, to prepare such a complex of the drug with the ion exchange resin so that the preparation is increased in size and the drug is diluted. Moreover, in a study using beagle dogs, the inventors of this invention found that the complexing of a drug with an ion exchange resin resulted in a reduction in the rate of drug dissolution so that the gastrointestinal absorbability of the drug is lowered.

SUMMARY OF THE INVENTION

Therefore, it is an object of the present invention to provide a solid preparation characterized by an effective mitigation of the bitterness or other unpleasant taste and/or odor of an active ingredient.

It is another object of the invention to provide a solid preparation wherein the leakage, liberation or diffusion of an active ingredient can remarkably be inhibited and the bitterness or other unpleasant taste and/or odor of said active ingredient can efficiently be mitigated.

It is a further object of this invention to provide a solid preparation wherein an efficient mitigation of the bitterness and others of the active ingredient as well as an easy ingestion or oral intake of the solid preparation can be realized.

It is a yet further object of the present invention to provide a solid preparation characterized by a significant mitigation of the bitterness or others of an active ingredient with a reduced amount of an ion exchanger.

Another object of the invention is to provide a solid preparation wherein the bitterness or others of an active ingredient can remarkably be mitigated with suppressing or inhibiting the formation of the complex of the active ingredient with an ion exchanger.

A further object of the present invention is to provide a solid preparation which is excellent in dissolution property and absorbability of the active ingredient in the digestive tract.

A yet further object of the invention is to provide a method of producing a solid preparation by which a solid preparation having improved mitigation of the bitterness or other unpleasant taste and/or odor of an active ingredient can be produced with easy and simple manner.

Another object of the invention is to provide a method of masking a taste or odor of a medicinally active ingredient.

The inventors of this invention found, after much research done to accomplish the above-mentioned objects, that when an ion exchanger is added to a clad powdery or granular preparation containing a medicinally active ingredient having an unpleasant taste and/or odor, the active ingredient liberated from said clad preparation is efficiently entrapped, with the result that the unpleasant taste and/or odor is remarkably mitigated without affecting the dissolution property and absorbability of the active ingredient. The present invention has been accomplished on the basis of the above findings.

Accordingly, the solid preparation of this invention comprises (A) a clad powdery or granular preparation containing a medicinally active ingredient and (B) a powdery or granular ion exchanger.

The medicinally active ingredient may have, for example, an unpleasant taste or odor.

Said clad powdery or granular preparation may for example be a matrix-based preparation or a coated preparation coated with a coating composition. The carrier of the matrix-based preparation may be an excipient, a binder, a disintegrator or the like. As examples of the coating composition, a water-soluble polymer, an enteric polymer, an acid-soluble polymer, a water-insoluble polymer and so on may be employed.

The above-mentioned ion exchanger may also include a cation exchange resin and an anion exchange resin. Said powdery or granular ion exchanger can have a mean particle size or diameter of finer or less than that of the clad powdery or granular preparation.

According to the method of the present invention, said powdery or granular preparation containing a medically active ingredient is blended with an ion exchanger to produce a solid preparation.

The present invention further provides a method of masking a taste or odor of a medicinally active ingredient which comprises allowing a powdery or granular preparation containing a medicinally active ingredient having a taste or odor to be co-existent with a powdery or granular ion exchanger.

DETAILED DESCRIPTION OF THE INVENTION

The term "clad" powdery or granular preparation (hereinafter referred to briefly as clad preparation) is used in this specification to mean not only a coated preparation obtained by coating a medicinally active ingredient or a preparation containing said ingredient with a coating composition but also a preparation in which the active ingredient is isolated from, or suppressed to contact with the ion exchanger in a varying manner, for example a matrix-based preparation such that a medicinally active ingredient is embedded in a matrix and a capsule such that a medicinally active ingredient is encased in a capsule shell, to name but a few examples.

The term "cladding material" as used herein means not only a coating composition in the narrow sense of the term but also any pharmaceutically acceptable material that attaches or adheres to a medicinally active ingredient to form a barrier between the active ingredient and ion exchanger according to each particular preparation, thus including, for example, capsule bases for capsules, carriers including binders used as a matrix base for a matrix-based preparation, and other additives.

The term "powdery or granular preparation" means to include powders having a mean particle size or diameter of 10 to 500 μm, and granules having a mean particle size or diameter of 500 to 1,500 μm. The term "powder" is used in this specification to mean any preparation such that all of its constituent particles pass through a sieve No. 18 (850 μm) in particle size analysis and 5% or less of its constituent particles does not pass and remains on a sieve No. 30 (500 μm). The term "fine granule" means any preparation of said powders such that 10% or less of the constituent particles pass through a sieve No. 200 (75 μm), and mean particle size or diameter thereof ranges from 75 to 500 μm. The term "granule" is used herein to mean any preparation wherein the whole constituent particles pass through a sieve No. 10 (1,700 μm), 5% or less of the whole particles does not pass and remains on a sieve No. 12 (1,400 μm), and 15% or less of the whole passes through a sieve No. 42 (355 μm).

The medicinally active ingredient may be any medicinal substance without regard to categories of clinical efficacy or indication. A medicinal substance having a taste and/or odor, especially having an unpleasant taste or odor, may advantageously be employed as the medicinally active ingredient. The unpleasant taste is any taste that elicits an objectionable sensation in the oral cavity when taken perorally, such as a bitter, pungent or acid taste or a compound taste consisting of such tastes. The most representative unpleasant taste is bitterness. The unpleasant odor includes a broad spectrum of odors which elicit unpleasant olfactory sensations in man or give discomfort to man.

Such medicinally active ingredients include, among others, various antibiotics [e.g. penicillin antibiotics such as carbenicillin indanyl sodium, bacampicillin, etc.; penem antibiotics such as acetoxymethyl (+)-(5R, 6S)-6-[(R)-1-hydroxyethyl]-3-(3-pyridyl)-7-oxo-4-thia-1-azabicyclo[3.2.0]hept-2-ene-2-carboxylate (hereinafter briefly referred to as TMA-230), etc.; cephem antibiotics such as cefaclor, cefotiam hexetil hydrochloride, cefteram pivoxil, cefpodoxime proxetil, etc.; macrolide antibiotics such as erythromycin, clarithromycin, etc.; tetracycline antibiotics such as tetracycline etc.; and other antibiotics such as chloramphenicol etc.]; pyridonecarboxylic acid synthetic antimicrobial agents such as enoxacin, sparfloxacin, etc.; cardiovascular agents such as delapril hydrochloride, meclofenoxate hydrochloride, diltiazem hydrochloride, etc; hypnotics such as estazolam etc.; cerebral circulation improving agents such as vinpocetine etc.; antianxiety drugs such as chlordiazepoxide, diazepam, etc.; vitamins such as fursultiamine, thiamine hydrochloride, calcium pantothenate, etc.; therapeutic agents for peptic ulcer such as cimetidine, pirenzepine hydrochloride, etc.; bronchodilators such as theophylline etc.; antimalarial agents such as quinine hydrochloride etc.; cardiotonics such as etilefrine hydrochloride etc.; antiarrhythmic agents such as propranolol hydrochloride, alprenolol hydrochloride, etc.; antihistaminics such as promethazine hydrochloride, diphenhydramine hydrochloride, etc.; antipyretic-antiinflammatory agents such as benzidamine hydrochloride etc.; antidiarrheal agents such as loperamide hydrochloride etc.; gastrointestinal prokinetic agents such as de(N-methyl)-N-isopropyl-8,9-anhydroerythromycin A 6,9-hemiacetal etc.; central nervous system drugs such as bifemelane hydrochloride, etc.; psychotropic agents such as nortriptyline hydrochloride, etc. The medicinally active ingredient further includes various compounds with inhibited oxidation or decomposition and various prodrugs prepared by subjecting active ingredients to partial chemical modification for improved intra-gastric stability and so forth.

The medicinally active ingredient having an unpleasant taste and/or odor may frequently have a basic group. As examples of said basic group, there may be mentioned an amino group; a hydrazino group; an amidino group; a guanidino group; a nitrogen-containing heterocyclic group such as pyrrolidinyl, piperidyl, morpholinyl, piperazinyl, imidazolyl, benzimidazolyl, pyrazolyl, pyridyl, pyrazinyl, pyrimidinyl, pyridazinyl, quinolyl, isoquinolyl, quinazolinyl, quinoxalinyl, purinyl and indolyl groups. These basic groups may optionally be substituted. Examples of such substituent include a $C_{1-6}$ alkyl group (e.g. methyl, ethyl, n-propyl i-propyl, n-butyl, hexyl, etc.), a $C_{1-6}$ alkoxy group (e.g. methoxy, ethoxy, propoxy, hexyloxy, etc.), a halogen atom (e.g. fluorine, chlorine, bromine or iodine) and the like.

The present invention is particularly suited for medicinally active ingredients having bitter tastes among the above-mentioned drugs. Such medicinally active ingredients include antibiotics (e.g. β-lactam antibiotics such as penicillin antibiotics, penem antibiotics, cephem antibiotics and others). Among these β-lactam antibiotics, those having basic groups such as amino and pyridyl, which may be substituted with such a substituent as mentioned above, and having strongly bitter tastes, for example the above-mentioned TMA-230 and cefotiam hexetil hydrochloride, are particularly suited for the practice of the invention.

In the present invention, said medicinally active ingredient is contained in the clad powdery or granular preparation.

Referring to the matrix-based preparation (a) comprising a matrix base and a medicinally active ingredient embedded therein, the matrix base as a cladding material includes a variety of carriers which are generally used in the field of pharmaceutical preparation, e.g. excipients such as lactose, sucrose, mannitol, corn starch, talc, crystalline cellulose, magnesium stearate, silicic anhydride, magnesium carbonate, calcium carbonate, L-cysteine, etc.; binders such as α-starch, partially α-starch, gelatin, gum arabic powder, methylcellulose, carmellose, carmellose sodium, hydroxypropylcellulose, hydroxypropylmethylcellulose, polyvinylpyrrolidine, pullulan, dextrin, etc., and disintegrators such as carmellose calcium, low-substituted hydroxypropylcellulose, crosscarmellose sodium, starch and so on.

The matrix-based preparation may further contain various additives, e.g. surfactants including anionic surfactants such as sodium alkyl sulfates etc. and nonionic surfactants such as polyoxyethylene sorbitan fatty acid esters and polyoxyethylene fatty acid esters, etc.; coloring agents such as tar colors, iron sesquioxide, yellow iron sesquioxide, titanium dioxide, etc.; corrigents such as saccharin, aspartame, menthol, etc.; adsorbents, preservatives, wetting agents, destaticizers, disintegration retardants and so on.

Among the above-mentioned carriers, the excipient and binder are often used and the disintegrator is also used in many cases. The amount of the carrier can be selected from within the range not interfering with the release and absorbability of the active ingredient, taking into consideration the intensity of bitterness, for instance, of the active ingredient. For example, the total amount of the carrier based on 100 parts by weight of the active ingredient may be about 1 to 50,000 parts by weight, preferably about 100 to 3,000 parts by weight and more preferably about 300 to 2,500 parts by weight. The proportion of the excipient may for example be about 10 to 99 weight %, preferably about 20 to 95 weight %, of the whole carrier and the proportion of the binder may for example be about 5 to 70 weight % and preferably about 10 to 50 weight % on the same basis.

In the above matrix-based preparation (a), the medicinally active ingredient may occur as dispersed in the matrix. The preparation containing an active ingredient in a matrix may be any of a kneaded powder, a granulated preparation, or other preparations. The dosage form of said preparation may be, for example, powders, fine granules, granules, pills, etc. Said matrix-based preparation (a) is often supplied as a granulated preparation and the dosage form thereof is frequently fine granules or granules.

The above preparation can be manufactured by the conventional processes. Thus, a kneaded powder can be manufactured by, for example, kneading the medicinally active ingredient with the binder and solvent (e.g. water), optionally together with an excipient and other additives, drying the kneaded mixture and pulverizing it as necessary. Granulated powder can be prepared by, for example, granulating the medicinally active ingredient, carrier and optional additives by the conventional kneading method, extrusion granulation method, fluidized-bed granulation method, spray granulation method, rotary granulation method (e.g. centrifugal granulation method using seed grains) or the like to provide fine granules, granules or pills. The granulation process may be a wet process using water or an organic solvent such as alcohol, or a dry process.

In the granulation of the medicinally active ingredient which is liable to be deactivated by heat, a wet process such as centrifugal granulation can be employed with advantage. For example, in the manufacture of the above preparation by centrifugal granulation, a centrifugal granulation machine is charged with seed particles (such as granulated sugar with an average particle size of about 100 to 300 μm) and while the machine is driven and a solution of the binder is introduced in a mist form, the powder containing the medicinally active ingredient together with optional excipient and other additives is introduced and caused to adhere to the seed particles. The resulting fine granules are dried and sieved to provide a coated preparation of fine granules.

The capsules (b) containing a medicinally active ingredient within capsule shells may be microcapsules or capsules obtained by filling capsule shells with the medicinally active ingredient or said fine granules or granules. Microcapsules can be used advantageously in many cases.

The microcapsules can be manufactured by cladding the surface of the medicinally active ingredient with a film-forming capsule base as a cladding material utilizing the coacervation, interfacial polymerization, fluidized-bed coating, spray granulation or other method. The capsule base may suitably be selected from the following coating compositions or agents used for the coated preparation (c).

The coating composition or agent that can be used as a cladding material for the coated preparation (c) includes macromolecular substances such as water-soluble polymers, water-insoluble polymers, acid-soluble polymers and enteric polymers. The water-soluble polymers mentioned above include gum arabic powder, gelatin, sodium alginate, methylcellulose, carmellose, carmellose sodium, hydroxypropylcellulose, hydroxyethylcellulose, hydroxypropylcellulose, polyvinylpyrrolidone, polyvinyl alcohol and pullulan, among others. The water-insoluble polymers include ethylcellulose, low-substituted hydroxypropylcellulose, aminoalkyl methacrylate copolymer, shellac and wax, among others. The acid-soluble polymers include polyvinylacetal diethylaminoacetate, among others. The enteric polymer mentioned above includes carboxymethylethylcellulose, hydroxypropylmethylcellulose phthalate, hydroxypropylmethylcellulose acetate succinate, acrylic copolymers, methacrylic copolymers, cellulose acetate phthalate and so on.

These coating compositions can be used alone or in combination. The preferred coating agent includes those film-forming polymers which do not affect the dissolution property or releasability of the active ingredient and yet preclude or suppress contact of the active ingredient with the ion exchanger, such as water-soluble polymers and enteric polymers.

The coating composition may contain various additives such as said surfactants, plasticizers, coloring agents, corrigents, adsorbents, preservatives, wetting agents, destaticizers, disintegration retardants, etc.

The coated preparation described above can be obtained by direct coating of the medicinally active ingredient but is generally prepared by coating said granulated preparation of the matrix-based preparation (a). In the coated preparation, said active ingredient and granulated preparation of the matrix-based preparation (a) and the like coated with a coating composition may be hereinafter referred to as a "coating load".

The amount of the coating composition (agent) can be adequately selected from within the range not interfering with the dissolution property or releasability and absorbability of the active ingredient according to the type of the active ingredient. For example, the coating agent may be used in a proportion of about 1 to 1,000 parts by weight, preferably about 5 to 100 parts by weight, based on 100 parts by weight of the coating load. The using amount of the coating composition is about 1 to 90% by weight, preferably about 5 to 50% by weight and more preferably about 7 to 30% by weight based on the total weight of the coated preparation. When the proportion of the coating composition is too small, the required amount of the ion exchanger is increased. Conversely, when it is too large, the rate of the dissolution or release and absorbability of the active ingredient tend to be decreased.

The coated preparation (c) can be manufactured by the conventional technology, for example by charging a fluidized-bed coating equipment with the active ingredient or granulated preparation of the matrix-based preparation (a) and so on and drying the charge under fluidization and spray-application of the coating composition containing optional additives and sieving the product.

The preferred clad powdery or granular preparation for use in this invention includes preparations insuring reductions in the exposed area of the active ingredient over the surface of the preparation, such as the above-mentioned granulated preparation of the matrix-based preparation (a), the capsules (b) and, in particular, the coated preparation (c). With such a preparation, the carrier, capsule base or coating composition suppresses the leakage of the active ingredient from the preparation to mitigate the unpleasant taste and odor to a certain extent and, at the same time, inhibits or suppresses the formation of the complex due to the contact of the active ingredient with the ion exchanger. Particularly the coated preparation obtained by coating said matrix-based preparation containing the active ingredient with a coating composition insures not only a marked inhibition of the leakage of the active ingredient but also a positive inhibition or suppression of the contact of the active ingredient with the ion exchanger. Therefore, with a small amount of the ion exchanger, the unpleasant taste and odor can be significantly controlled or mitigated.

Preferred form of the clad preparation includes powders, fine granules, granules, pills and microcapsules and, in many cases, is fine granules, granules or microcapsules.

Preferred examples of the clad powdery or granular preparation of the invention include preparations having mean particle sizes or diameters of about 10 to 1,500 μm, more preferably about 50 to 1,500 μm and particularly about 100 to 1,500 μm.

The ion exchanger which can be used in this invention includes cation exchange resins and anion exchange resins. Among the cation exchange resins may be reckoned styrenic strongly acidic cation exchange resins [e.g. Diaion SK110 (ion exchange capacity: 2.0 meq/ml or more), Mitsubishi Kasei Corporation, Japan], methacrylic weakly acidic cation exchange resins [e.g. Diaion WK10 (ion exchange capacity: 2.5 meq/ml or more), Mitsubishi Kasei Corporation, Japan], acrylic weakly acidic cation exchange resins [e.g. Diaion WK20 (ion exchange capacity: 3.5 meq/ml or more), Mitsubishi Kasei Corporation, Japan], methacrylic copolymers (Eudragit L100, Eudragit L100-55; Rohm-Pharma), carboxyvinyl polymers [Carbopol, Showa Denko, Japan; Hi Vis Wako, Wako Pure Chemical Industries, Japan], etc.; and inorganic cation exchangers such as zeolite, fuller's earth, peat, lignite, synthetic zeolite, permutite, zirconium tungstate, etc.

The anion exchanger includes styrenic strongly basic anion exchange resins [Diaion SAN 1, Mitsubishi Kasei Corporation, Japan; etc.], styrenic weakly basic anion exchange resin [Amberlite IR 45, Rohm & Haas Co.; etc.], acrylic weakly basic anion exchange resins Diaion WA10, Mitsubishi Kasei Corporation, Japan; etc.] and inorganic anion exchangers such as dolomite, iron oxide hydrate gel, zirconium oxide hydrate gel, activated carbon, etc.

These ion exchangers can be selectively used according to the kinds of functional groups possessed by the medicinally active ingredient. For example, a cation exchanger is used with advantage when the medicinally active ingredient has a basic group, and an anion exchanger is used with advantage when the active ingredient has an acidic group.

The preferred ion exchanger includes. cation exchange resins and anion exchange resins. Many of the medicinally active ingredients having unpleasant tastes and odors have basic groups. Therefore, in the practice of this invention, cation exchangers and particularly cation exchange resins having comparatively more effective ion exchange capacities are frequently employed The ion exchanger is used in a powdery or granular form. Unless its drug-trapping potential is adversely affected, the ion exchanger can be formulated with an excipient, disintegrator, binder, surfactant, coloring agent and other additives and put to use as, for example, fine granules or granules. As the excipient, disintegrator, binder, etc., those mentioned hereinbefore can be employed. Such a composition of the ion exchanger can be produced by the various procedures as described hereinbefore, for example by kneading, extrusion granulation, centrifugal granulation, etc.

The size of the ion exchanger or its composition can be liberally selected from within the range insuring an efficient entrapment of the leaked or liberated active ingredient and not adversely affecting the ease of ingestion or intake and is generally about 0.1 to 1,000 μm, preferably about 0.5 to 500 μm and more preferably about 1 to 100 μm in mean particle size or diameter. The ion exchanger of a mean grain or particle diameter of about 10 to 50 μm is frequently employed. The ion exchanger may be used in a pulverized form in many cases.

The preferred powdery or granular ion exchanger includes ion exchangers having mean particle diameters smaller or finer than the mean particle diameter of said clad preparation. The ratio of the mean particle diameter Dp of the clad preparation to the mean particle diameter Di of the powdery or granular ion exchanger is such that Dp/Di equals about 1/0.001 to 0.8, preferably Dp/Di equals about 1/0.01 to 0.5 and more preferably Dp/Di equals about 1/0.02 to 0.5. Specifically, said ratio is frequently such that Dp/Di equals about 1/0.04 to 0.3. The solid preparation comprising such ion exchanger is excellent not only in an extremely efficient entrapment of the leaked or liberated active ingredient e.g. in oral cavity but also in an easy ingestion or oral intake.

The specific surface area of the ion exchanger may, for example, be about 0.1 to 20 $m^2/g$, preferably about 0.3 to 10 $m^2/g$ and, for still better results, about 0.5 to 5 $m^2/g$.

The exchange capacity of the ion exchanger may be varied according to species of the ion exchanger and is usually about 0.1 to 10 meq/ml. The exchange capacity of the ion exchange resin to be used as the ion exchanger is, for instance, about 1 to 5 meq/ml.

The amount of the powdery or granular ion exchanger in the solid preparation of the invention can be selected according to various factors such as the physicochemical properties of the medicinally active ingredient, ion exchange capacity and grain size of the ion exchanger. The amount of the ion exchanger based on 100 parts by weight of said clad preparation is about 1 to 500 parts by weight, preferably about 2 to 200 parts by weight and more preferably about 3 to 180 parts by weight, and for still better results, about 5 to 150 parts by weight. The ion exchanger is employed, in many cases, in a proportion of about 8 to 80 parts by weight, especially about 10 to 50 parts by weight based on 100 parts by weight of the clad preparation.

Relative to the medicinally active ingredient contained in said clad preparation, the amount of the ion exchanger is for instance about 10 to 5,000 parts by weight, preferably about 100 to 3,000 parts by weight and more preferably about 150 to 2,000 parts by weight. For still better results, about 200 to 1,500 parts by weight and particularly about 250 to 1,000 parts by weight of the ion exchanger based on 100 parts by weight of said active ingredient can frequently be used.

In the solid preparation of the present invention, the equivalent ratio Ci/Cp of the total amount of the exchange group Ci of the powdery or granular ion exchanger to the amount of ion exchangeable group (an acidic group or a basic group) Cp of said active ingredient contained in the clad preparation may be 1 or more (for example, about 1 to 50). Even when the ratio Ci/Cp is, however, less than 1, for example about 0.05 to 0.8, particularly about 0.05 to 0.4, the unpleasant taste and odor of the active ingredient can remarkably be mitigated.

The solid preparation of the present invention needs only to comprise said clad preparation and said powdery or granular ion exchanger. In the solid preparation of this invention, said clad preparation and said powdery or granular ion exchanger may be co-existent without being mixed. In the preferred solid preparation, at least a part of said powdery or granular ion exchanger occurs covering, touching, attaching or adhering to the surface of said clad preparation. In such solid preparation as above, the active ingredient liberated or leaked from the clad preparation can efficiently be trapped by the ion exchanger attached or adhered to the solid preparation, therefore the unpleasant taste and odor of the active ingredient can efficiently be mitigated or reduced.

The solid preparation of this invention is characterized in that even if the amount of the ion exchanger is only about 1 to 100 parts by weight based on 100 parts by weight of said clad preparation or only about 10 to 500 parts by weight based on 100 parts by weight of the medicinally active ingredient, the unpleasant taste and odor of the active ingredient can be remarkably reduced and that, yet, the drug dissolution or release kinetics of the preparation in the digestive tract is not adversely affected.

Thus, since the leakage, liberation or diffusion of the active ingredient is inhibited or suppressed by the barrier cladding in the solid preparation of the invention, even when a small amount of the ion exchanger is used, said ion exchanger can efficiently trap the active ingredient liberated from the clad preparation. Therefore, even when the amount of the medicinally active ingredient in the unit dosage form is large, the unpleasant taste and odor attributable to the active ingredient are mitigated to improve the palatability of the preparation, thus making it easier for children and the aged to take and, hence, leading to improved compliance. Moreover, the preparation is not increased in bulk.

Furthermore, because the direct contact of the ion exchanger and the active ingredient is avoided or suppressed in the preparation, the rate of complex formation between the active ingredient and the ion exchanger is minimized. As a consequence, unlike the case with the preparation proposed by British Patent 1462356, the dissolution and absorbability of the active ingredient are not reduced, thus providing for high and sustained bioavailability.

The solid preparation of the present invention can be manufactured by, for example, blending or mixing said clad preparation with said ion exchanger, optionally together with various additives (e.g. fluidizing agents such as talc and light silicic acid anhydride and destaticizers). The powdery or granular ion exchanger can be rendered covering, touching, attaching or adhering to the surface of said clad preparation by such blending or mixing. Further, in the solid preparation of the present invention, the dissolution and absorbability of the active ingredient in the digestive tract are not reduced by the blending or mixing, since the direct contact of the ion exchanger with the active ingredient can be avoided or suppressed and the rate of the complex formation can remarkably be minimized in the preparation.

For the blending or mixing of the clad preparation with the ion exchanger, a variety of mixers can be employed. For instance, a mixer which gives a high shearing force can be used for the blending or mixing. In the solid preparation of the present invention, a high bioavailability can be maintained or sustained even when such a mixer giving a high shearing force is used, since the contact of the ion exchanger with the active ingredient can be avoided or inhibited in such blending or mixing under a high shearing force, thus the rate of the formation of the complex can markedly be reduced.

The mixture of clad preparation and the ion exchanger can be packed or charged into divided packages. Said mixture can also be packed or charged into capsules with the use of a capsule-filling machine.

The above clad preparation-ion exchanger composition can be supplemented with appropriate additives, such as an excipient, binder, disintegrator and lubricant, and compression-molded to provide tablets. In such cases, two or more species of the above-mentioned mixture containing the clad preparations different in solubilities or comprising incompatible drugs may be tabletted into tablets having two or more layers. These tablets having multiple layers may be sandwich-type tablets having a buffering layer between each layer. The buffering layer may be a thin layer.

Tablets can be prepared by compression-molding the clad preparation and the ion exchanger into tablets having two or more layers wherein each different adjacent layer comprises different ingredient, that is, said tablets have a layer comprising the clad preparation and a layer comprising the ion exchanger separately therein.

Moreover, these tablets may be film-coated. This coating operation can be carried out by the conventional technology, for example by means of an air-aided coating machine. As the coating material, the coating compositions, coloring agents, etc. mentioned hereinbefore can be employed.

The solid preparation thus obtained according to this invention can be orally administered not only as it is, but also in the form of an aqueous suspension or a syrup suspension. The pharmacologic effects, indications, dosage and safety of the solid preparation of this invention are not different from those of the medicinally active ingredient contained therein.

EXAMPLES

The following examples, comparative examples and experimental examples are merely intended to illustrate this invention in further detail and should by no means be construed as defining the scope of the invention.

Comparative Example 1

According to the formulation shown below, fine granules were prepared by means of a centrifugal granulator [CF160, Freund Industrial Co.]. First, the granulator was charged with 189.0 g of granulated sugar SR-60-80 (mean grain size 210 μm) as seed particles. Then, under the operating conditions of 500 rpm, air temperature 25° C. and slit air pressure 0 4 Kg/cm²150.0 g of 2% hydroxypropylcellulose [HPC-L, Nippon Soda Co., Japan]-ethanol was introduced from the spray nozzle means at delivery pressure 0.4 Kg/cm² and delivery rate 1.5 g/min and a mixed powder of 15.0 g of TMA-230, a penem antibiotic, and 93.0 g of milled granulated sucrose was introduced. The clad preparation thus obtained was dried in vacuo at 25° C. for 16 hours and, then, sieved by using No. 30 (500 μm) and No. 200 (75 μm) circular sieves to provide fine granules A (mean particle diameter 380 μm).

| Fine granules A (Comparative Example 1) | |
| --- | --- |
| Granulated sugar SR-60-80 | 189.0 g |
| TMA-230 | 15.0 g |
| Milled granulated sugar | 93.0 g |
| Hydroxypropylcellulose (HPC-L) | 3.0 g |
| Ethanol | 147.0 g |
| Total | 300.0 g |

Comparative Examples 2 and 3

The fine granules A thus obtained in Comparative Example 1 were coated with an enteric coating composition of the following formulation to provide a batch of enteric-coated fine granules. Thus, a fluidized-bed granulation dryer (FD-3S, Worster process, Powrex Corporation, Japan) was charged with 200.0 g of the above fine granules A and the enteric coating composition was introduced from spray nozzle means at air temperature 50° C., air delivery rate 0.8 m3/min. and spray pressure 1.2 Kg/cm² to prepare two kinds of enteric fine granules with the coating amounts of 10 weight % and 20 weight %, respectively, on a solids basis, relative to said fine granules A (hereinafter referred to as 10%-coating enteric fine granules and 20%-coating enteric fine granules, respectively). These enteric fine granules were sieved by using No. 30 (500 μm) and No. 200 (75 μm) circular sieves to provide granules (mean particle diameter 400 μm).

| [Enteric coating composition] | |
| --- | --- |
| Hydroxypropylmethylcellulose phthalate | 95.0 g |
| Polyethylene glycol 6,000 | 5.0 g |
| Acetone | 1142.9 g |
| Ethanol | 285.7 g |
| Total | 1528.6 g |
| [10%-coating enteric fine granules (Comparative Example 2)] | |
| Fine granules A | 200.0 g |
| Hydroxypropylmethylcellulose phthalate | 19.0 g |
| Polyethylene glycol 6,000 | 1.0 g |
| Total | 220.0 g |
| [20%-coating enteric fine granules (Comparative Example 3)] | |
| Fine granules A | 200.0 g |
| Hydroxypropylmethylcellulose phthalate | 38.0 g |
| Polyethylene glycol 6,000 | 2.0 g |
| Total | 240.0 g |

Examples 1 to 4

Each of the above species of enteric fine granules obtained in Comparative Examples 2 and 3 was blended with a styrenic strongly acidic cation exchange resin [Diaion SK110, Mitsubishi Kasei Corporation, Japan] in a compact V-mixer [TM-4, Showa Scientific Co., Japan] for 5 minutes to provide four species of preparations of the under-mentioned compositions (Examples 1 to 4). The ion exchange resin was finely divided or pulverized [using an atomizer with a 1 mm φ screen] and dried in vacuo at 40° C. for 16 hours prior to use (mean particle diameter 40 μm).

| [Example 1] | |
| --- | --- |
| 10%-Coating enteric fine granules | 11.0 g |
| Diaion SK110 | 2.0 g |
| Total | 13.0 g |
| [Example 2] | |
| 10%-Coating enteric fine granules | 11.0 g |
| Diaion SK110 | 5.0 g |
| Total | 16.0 g |
| [Example 3] | |
| Diaion SK110 | 2.0 g |
| Total | 14.0 g |
| [Example 4] | |
| 20%-Coating enteric fine granules | 12.0 g |
| Diaion SK110 | 5.0 g |
| Total | 17.0 g |

Examples 5 and 6

The two preparations of the following formulae were obtained in the same manner as in Examples 1 to 4, except for using a methacrylic weakly acidic cation exchange resin [Diaion WK10, Mitsubishi Kasei Corporation, Japan], and an acrylic weakly acidic cation exchange resin [Diaion WK20, Mitsubishi Kasei Corporation, Japan] instead of the styrenic strongly acidic cation exchange resin [Diaion SK110, Mitsubishi Kasei Corporation, Japan]. The ion exchange resins to be employed were previously pulverized with the use of an atomizer with a 1 mm φ screen and dried in vacuo at 0° C. for 16 hours (mean particle diameter 55 μm).

| [Example 5] | |
| --- | --- |
| 10%-Coating enteric fine granules | 11.0 g |
| Diaion WK10 | 5.0 g |
| Total | 16.0 g |
| [Example 6] | |
| 10%-Coating enteric fine granules | 11.0 g |
| Diaion WK20 | 5.0 g |
| Total | 16.0 g |

Examples 7 to 10

The procedures of Examples 1 to 4 were repeated except that a methacrylic copolymer [Eudragit L100, Rohm-Pharma; mean particle diameter 3 μm] was employed instead of the styrenic strongly acidic cation exchange resin

[Diaion SK110, Mitsubishi Kasei Corporation, Japan] to obtain the four species of preparations of the following compositions.

[Example 7]

| | |
|---|---|
| 10%-Coating enteric fine granules | 11.0 g |
| Eudragit L100 | 5.0 g |
| Total | 16.0 g |

[Example 8]

| | |
|---|---|
| 10%-Coating enteric fine granules | 11.0 g |
| Eudragit L100 | 10.0 g |
| Total | 21.0 g |

[Example 9]

| | |
|---|---|
| 20%-Coating enteric fine granules | 12.0 g |
| Eudragit L100 | 5.0 g |
| Total | 17.0 g |

[Example 10]

| | |
|---|---|
| 20%-Coating enteric fine granules | 12.0 g |
| Eudragit L100 | 5.0 g |
| Total | 17.0 g |

Comparative Example 4

To 25.0 g of hydroxypropylcellulose [HPC-H, Nippon Soda Co., Japan] in a mortar were added 5.0 g of a penera antibiotic (TMA-230) and 70.0 g of milled granulated sucrose, and the mixture was added with 12 ml of purified water to be granulated. The resultant granules were dried in vacuo at 30° C. for 16 hours and sieved with the use of No. 30 (500 μm) and No. 200 (75 μm) circular sieves to provide fine granules B (mean particle diameter 410 μm).

| [Fine granules B (Comparative Example 4)] | |
|---|---|
| TMA-230 | 5.0 g |
| Milled granulated sugar | 70.0 g |
| Hydroxypropylcellulose (HPC-H) | 25.0 g |
| (Purified water | 12 ml) |
| Total | 100.0 g |

Example 11

The fine granules B thus obtained in Comparative Example 4 (10 g) was blended with 5 g of a styrenic strongly acidic cation exchange resin [Diaion SK110, Mitsubishi Kasei Corporation, Japan] in a compact V-mixer for 5 minutes to give a preparation. The ion exchange resins were finely pulverized using an atomizer with a 1 mm φ screen and dried in vacuo at 40° C. for 16 hours (mean particle diameter 40 μm).

| | |
|---|---|
| Fine granules B | 10.0 g |
| Diaion SK110 | 5.0 g |
| Total | 15.0 g |

Comparative Example 5

The above mentioned procedures of Comparative Example 4 were repeated except that cefotiam hexetil hydrochloride, a cephem antibiotic, was used instead of TMA-230 to prepare fine granules C (mean particle diameter 400 μm).

| [Fine granules C (Comparative Example 5)] | |
|---|---|
| Cefotiam hexetil hydrochloride | 5.0 g |
| Milled granulated sugar | 70.0 g |
| Hydroxypropylcellulose (HPC-H) | 25.0 g |
| (Purified water | 12 ml) |
| Total | 100.0 g |

Example 12

Example 11 was followed except for using the fine granules C instead of the fine granules B.

| | |
|---|---|
| Fine granules C | 10.0 g |
| Diaion SK110 | 5.0 g |
| Total | 15.0 g |

Examples 13 to 17

According to the formulation as below, fine granules of ion exchange resin were prepared by means of a centrifugal granulator [CF160, Freund Industrial Co.]. Thus, the granulator was charged with 150.0 g of granulated sugar SR-60-80 (mean particle diameter 210 μm) as seed particles. Under the operating conditions of rotary rate of 500 rpm, air temperature of 25° C., and slit air pressure of 0.4 Kg/cm$^2$, 94.5 g of 2% ethanol solution of hydroxypropylcellulose [HPC-L, Nippon Soda Co., Japan] was introduced from the spray nozzle means at a spray pressure of 0.4 Kg/cm$^2$ and delivery rate of 1.5 g/min, and a mixed powder of 60.0 g of a styrenic strongly acidic cation exchange resin [Diaion SK110, Mitsubishi Kasei Corporation, Japan] and 30.0 g of milled granulated sugar was sprayed and attached thereto to give fine granules D (mean particle diameter 320 μm).

| Fine granules D | |
|---|---|
| Granulated sugar SR-60-80 | 150.0 g |
| Diaion SK110 | 60.0 g |
| Milled granulated sugar | 30.0 g |
| Hydroxypropylcellulose (HPC-L) | 1.89 g |
| (Ethanol | 92.61 g) |
| Total | 241.89 g |

The fine granules B (10 g) obtained in Comparative Example 4 was blended with 0.5 to 10 g of the fine granules D containing the styrenic strongly acidic cation exchange resin [Diaion SK110] in a compact V mixer for 5 minutes to prepare five species of preparations. The ion exchange resins were previously pulvervized with the use of an atomizer with a 1 mm φ screen and dried in vacuo at 40° C. for 16 hours (mean particle diameter 40 μm).

| [Example 13] | | |
|---|---|---|
| Fine granules B | 10.0 g | |
| Fine granules D | 0.5 g | |
| (containing Diaion SK110 | 124 mg) | |
| Total | 10.5 g | |
| [Example 14] | | |
| Fine granules B | 10.0 g | |
| Fine granules D | 1.0 g | |
| (containing Diaion SK110 | 248 mg) | |
| Total | 11.0 g | |
| [Example 15] | | |
| Fine granules B | 10.0 g | |
| Fine granules D | 3.0 g | |
| (containing Diaion SK110 | 744 mg) | |
| Total | 13.0 g | |
| [Example 16] | | |
| Fine granules B | 10.0 g | |
| Fine granules D | 5.0 g | |
| (containing Diaion SK110 | 1240 mg) | |
| Total | 15.0 g | |
| [Example 17] | | |
| Fine granules B | 10.0 g | |
| Fine granules D | 10.0 g | |
| (containing Diaion SK110 | 2480 mg) | |
| Total | 20.0 g | |

Comparative Example 6

A penem antibiotic, TMA-230, (5.0 g) was blended with 93.0 g of milled granulated sugar and 2.0 g of hydroxypropylcellulose [HPC-L, Nippon Soda Co., Japan] in a mortar, and to the mixture was added 20 ml of purified water to give granules. The resultant granules were dried in vacuo at 30° C. for 16 hours and sieved by using No. 30 (500 µm) and No. 200 (75 µm) circular sieves to prepare fine granules E (mean particle diameter 370 µm).

| [Fine granules E (Comparative Example 6)] | |
|---|---|
| TMA-230 | 5.0 g |
| Milled granulated sugar | 93.0 g |
| Hydroxypropylcellulose (HPC-L) | 2.0 g |
| (Purified water | 20 ml) |
| Total | 100.0 g |

The following experimental examples and typical results thereof are illustrated to show the effects obtained by the samples as above.

Experimental Example 1

(Threshold for bitterness test)

Test procedure:

A penem antibiotic, TMA-230, and a cephem antibiotic, cefotiam hexetil hydrochloride, were respectively dissolved in purified water (deionized water) and a syrup solution (30% by weight aqueous solution of purified sucrose) in concentrations as shown in Tables 1 and 2. The resultant solution (10 ml) was administered to 10 volunteers (5 males and 5 females, aged 25- to 45-years-old) directly in oral cavity and remained therein for 20 seconds. The grade of feeling for bitterness or unpleasant odor was evaluated according to the following three criteria and the threshold was determined.

| Criteria | |
|---|---|
| −: | neither bitterness nor unpleasant odor was perceived |
| +/−: | slight bitterness was perceived |
| +: | severe bitterness or unpleasant odor was perceived |

Results:

Each solution was subjected to the above-mentioned sense evaluation and the ratios of volunteers who evaluated for "±" or "+" relative to the total numbers of the volunteers are shown in Tables 1 and 2. The evaluation results for TMA-230, a penem antibiotic, and for cefotiam hexetil hydrochloride, a cephem antibiotic, are respectively shown in Table 1 and Table 2.

TABLE 1

| Concentration (µg/ml) | Aqueous solution | Syrup solution |
|---|---|---|
| 10 | 0/10 | 0/10 |
| 50 | 0/10 | 0/10 |
| 80 | 0/10 | 0/10 |
| 100 | 4/10 | 0/10 |
| 200 | 7/10 | 0/10 |
| 500 | 10/10 | 5/10 |

TABLE 2

| Concentration (µg/ml) | Aqueous solution |
|---|---|
| 5 | 0/10 |
| 10 | 6/10 |
| 20 | 10/10 |
| 50 | 10/10 |

As shown in Tables 1 and 2, the threshold of bitterness for the penem antibiotic, TMA-230, was 100 µg/ml (500 µg/ml for the syrup solution), the threshold for the cephem antibiotic, cefotiam hexetil hydrochloride, was 10 µg/ml.

Experimental Example 2

(Change in time course of the dissolution of the medicinally active ingredient from the coated enteric fine granules, and mitigation effect of bitterness by the ion exchange resin)

Test procedure:

A test tube was charged with each sample (Examples 1 to 12 and Comparative Examples 2 to 5) in an amount corresponding to 50 mg of the penem antibiotic (TMA-230) and 10 ml of purified water (deionized water). The charged test tube was installed in a rotary shaker (ROTATOR, Taiyo Kagaku Kogyo Co., Japan) and rotated at 10 rpm for 2 hours. The charged was sampled during the rotation and the sampled was filtered. The filtrate was diluted with a mixture of phosphate buffer-acetonitrile [60/40(V/V)] and subjected to a high performance liquid chromatography to determine the content of TMA-230. Thus the dissolution rate was determined.

On the other hand, the procedures of detection by sense for bitterness and unpleasant odor in Experimental Example 1 were repeated using the sample sampled during the time course. Three male were tested, and the average evaluation was determined.

Results:

The variations of the dissolution rate and evaluation of bitterness during the test are shown in Tables 3 to 11. In Table 5 to 9, the number in the unit of "mg" signifies the weight of the ion exchange resin.

TABLE 3

| | Comparative Sample (Comparative Example 6) | |
|---|---|---|
| Time | Dissolution rate | Bitterness |
| 5 sec. | 65% | + |
| 10 sec. | 80% | + |
| 30 sec. | 99% | + |
| 3 min. | 100% | + |
| 10 min. | 100% | + |

Table 3 indicates the results for Comparative Sample (fine granules containing TMA-230: Comparative Example 6). The dissolution of the drug from the granules of Comparative Sample was extremely rapid and the bitterness was remarkably strong.

TABLE 4

| | Comparative Example 2 (10%-coating) | | Comparative Example 3 (20%-coating) | |
|---|---|---|---|---|
| Time | Dissolution rate | Bitterness | Dissolution rate | Bitterness |
| 30 sec. | 0% | − | 0% | − |
| 30 min. | 12% | +/− | 6% | − |
| 60 min. | 20% | + | 10% | +/− |
| 2 hr | 36% | + | 26% | + |

TABLE 5

| | Example 1 (200 mg) | | Example 2 (500 mg) | |
|---|---|---|---|---|
| Time | Dissolution rate | Bitterness | Dissolution rate | Bitterness |
| 30 sec. | 0% | − | 0% | − |
| 30 min. | 0.3% | − | 0% | − |
| 60 min. | 0.1% | − | 0% | − |
| 2 hr | 0.2% | − | 0% | − |

TABLE 6

| | Example 3 (200 mg) | | Example 4 (500 mg) | |
|---|---|---|---|---|
| Time | Dissolution rate | Bitterness | Dissolution rate | Bitterness |
| 30 sec. | 0% | − | 0% | − |
| 30 min. | 0% | − | 0% | − |
| 60 min. | 0% | − | 0% | − |
| 2 hr | 0% | − | 0% | − |

Tables 4 to 6 indicate the adding effect of the styrenic strongly acidic cation exchange resin on the dissolution of the medicinally active ingredient from the 10%- and 20%-coating enteric fine granules containing TMA-230 with the passage of time. Table 4 shows the results for Comparative Examples 2 and 3, Table 5 and Table 6 respectively indicate the results for Examples 1 and 2, and Examples 3 and 4.

The dissolution rate of the medicinally active ingredient from the 10%-coating enteric fine granules (Comparative Example 2) was 20% and 36% respectively after 1 hour and 2 hours from the initial of the test, and for the 20%-coating enteric fine granules (Comparative Example 3), the dissolution rate was independently 10% and 26% after 1 hour and 2 hours from the initial of the test. Thus, the dissolution rates were increased with the passage of time accompanied with bitterness being increased or enhanced. To the contrary, in the samples incorporated with the ion exchange resins (Examples 1 to 4), the released or dissoluted medicinally active ingredient was trapped, thus the apparent dissolution rate was suppressed and the bitterness was mitigated for a longer duration.

TABLE 7

| | Example 5 (WK10) (500 mg) | | Example 6 (WK20) (500 mg) | |
|---|---|---|---|---|
| Time | Dissolution rate | Bitterness | Dissolution rate | Bitterness |
| 30 sec. | 0% | − | 0% | − |
| 30 min. | 1% | − | 2% | − |
| 60 min. | 2% | − | 3% | − |
| 2 hr | 3% | − | 4% | − |

Table 7 shows the adding effect of the weakly acidic cation exchange resin (Diaion WK10, Diaion WK20) on the dissolution of the medicinally active ingredient from the 10%-coating enteric fine granules containing TMA-230 with the elapse of the time (Examples 5 and 6). By means of the addition of the weakly acidic cation exchange resin, the apparent dissolution rate was suppressed and the bitterness was mitigated.

TABLE 8

| | Example 7 (500 mg) | | Example 8 (1000 mg) | |
|---|---|---|---|---|
| Time | Dissolution rate | Bitterness | Dissolution rate | Bitterness |
| 30 sec. | 0% | − | 0% | − |
| 30 min. | 5% | − | 11% | − |
| 60 min. | 10% | − | 14% | +/− |

TABLE 9

| | Example 9 (500 mg) | | Example 10 (1000 mg) | |
|---|---|---|---|---|
| Time | Dissolution rate | Bitterness | Dissolution rate | Bitterness |
| 30 sec. | 0% | − | 0% | − |
| 30 min. | 4% | − | 5% | − |
| 60 min. | 7% | − | 8% | − |

Tables 8 and 9 show the adding effect of the methacrylic copolymer (Eudragit L100) on the dissolution of the medicinally active ingredient from the 10%- and 20%-coating enteric fine granules with the passage of time (Examples 7 to 10). Although being slightly lower than those of the strongly acidic and weakly acidic cation exchange resins as mentioned above, the mitigating effect of said copolymer on bitterness was superior to that of the granules without ion exchange resin.

TABLE 10

| Time | Comp. Ex. 4 Bitterness | Example 11 Bitterness |
| --- | --- | --- |
| 10 sec. | + | − |
| 30 sec. | + | +/− |
| 3 min. | + | + |
| 10 min. | + | + |

The adding effects of the styrenic strongly acidic cation exchange resin on the dissolution of the medicinally active ingredient from the fine granules containing TMA-230 with passage time are shown in Table 10. In the TMA-230-containing fine granules without the addition of the ion exchange resin (Comparative Example 4), the bitterness was sensed or detected from the initial of the trial, on the contrary, in the sample added with the ion exchange resin (Example 11), the bitterness was effectively mitigated on the early stage.

TABLE 11

| Time | Comp. Ex. 5 Bitterness | Example 12 Bitterness |
| --- | --- | --- |
| 10 sec. | + | +/− |
| 30 sec. | + | +/− |
| 3 min. | + | + |
| 10 min. | + | + |

Table 11 shows the effect of the addition of the styrenic strongly acidic cation exchange resin on the dissolution or releasing of the medicinally active ingredient from the fine granules containing cefotiam hexetil hydrochloride with the elapse of time. For the cefotiam hexetil hydrochloride-containing fine granules (Comparative Example 5), the bitterness was developed in the early stage, but for the sample added with the ion exchange resin (Example 12), the bitterness was suppressed in the initial stage.

Experimental Example 3

(The suppressing effect of the addition of ion exchange resins on the dissolution of the medicinally active ingredient from fine granules containing the medicinally active ingredient)

Test procedures:

A 50-ml measuring flask was charged with each sample (Comparative Example 1 and Examples 13 to 17) in an amount in terms of 50 mg of the penem antibiotic (TMA-230). The charged was added with purified water (deionized water) and shaken for 10 minutes. After shaking, distilled water was added up to the exact total volume of 50 ml, and the mixture was filtrated (screen size 0.45 μm). The filtrate (1 ml) was diluted up to 50 ml with a mixture of phosphate buffer/acetonitrile [60/40 (V/V)], and subjected to high performance liquid chromatography to measure the content of TMA-230. The dissolution rate was thus determined.

Results:

The dissolution rates of said medicinally active ingredient in each sample are shown in Table 12.

TABLE 12

| No. | Adding amount of fine granules of ion exchange resin (mg) | Dissolution rate (%) |
| --- | --- | --- |
| Comp. Ex. 1 | 0 (0) | 99.1 |
| Ex. 13 | 50 (12.4) | 80.4 |
| Ex. 14 | 100 (24.8) | 70.2 |
| Ex. 15 | 300 (74.4) | 31.5 |
| Ex. 16 | 500 (124.0) | 4.6 |
| Ex. 17 | 1000 (248.0) | 0.4 |

The amounts indicated in "( )" are the amounts in terms of the ion exchange resin.

As clearly shown in Table 12, the apparent releasing of the medicinally active ingredient from the fine granules containing the same was suppressed even when the ion exchange resin was added in the form of preparation of fine granules. The optimum adding amount in such case is assumed to be about 2 to 3 times as large as that of the medicinally active ingredient.

The results of the experimental examples reveal that the solid preparation of the present invention can remarkably decrease or mitigate the bitterness and unpleasant odor of the medicinally active ingredients even when using a small amount of the ion exchanger.

What is claimed is:

1. A solid preparation comprising (A) a clad powdery or granular preparation containing a medicinally active ingredient and (B) a powdery or granular ion exchanger, wherein the ion exchanger and the active ingredient are not in direct contact.

2. A solid preparation comprising (A) a clad powdery or granular preparation containing a medicinally active ingredient having an unpleasant trade or odor and (B) a powdery or granular ion exchanger, wherein the ion exchanger and the active ingredient are not in direct contact.

3. A solid preparation according to claim 2 wherein said medicinally active ingredient has a basic group.

4. A solid preparation according to claim 2 wherein said medicinally active ingredient is a β-lactam antibiotic.

5. A solid preparation according to claim 4 wherein said β-lactam antibiotic has a basic group.

6. A solid preparation according to claim 2 wherein said clad powdery or granular preparation is a matrix-based preparation or a coated preparation coated with a coating composition.

7. A solid preparation according to claim 6 wherein the carrier of the matrix-based preparation is at least one member selected from the group consisting of an excipient, a binder and a disintegrator.

8. A solid preparation according to claim 6 wherein the amount of the carrier of the matrix-based preparation is 1 to 50,000 parts by weight based on 100 parts by weight of the medicinally active ingredient.

9. A solid preparation according to claim 6 wherein said coating composition comprises a water-soluble polymer, an enteric polymer, an acid-soluble polymer or a water-insoluble polymer.

10. A solid preparation according to claim 6 wherein the amount of the coating composition is 1 to 90% by weight based on the total weight of the coated preparation.

11. A solid preparation according to claim 2 wherein the mean particle diameter of said clad powdery or granular preparation is 10 to 1,500 μm.

12. A solid preparation according to claim 2 wherein said ion exchanger is a cation exchange resin or an anion exchange resin.

13. A solid preparation according to claim 12 wherein said cation exchange resin is at least one member selected from the group consisting of a styrenic strongly acidic cation exchange resin, a methacrylic weakly acidic cation exchange resin, an acrylic weakly acidic cation exchange resin, a methacrylic copolymer and a carboxyvinyl polymer.

14. A solid preparation according to claim 2 wherein the mean particle diameter of said powdery or granular ion exchanger is 0.1 to 1,000 μm.

15. A solid preparation according to claim 2 wherein the mean particle diameter of the powdery or granular ion exchanger is finer than that of the powdery or granular medicinally active ingredient.

16. A solid preparation according to claim 2 wherein the specific surface area of said ion exchanger is 0.1 to 20 m$^2$/g.

17. A solid preparation according to claim 2 which comprises 10 to 5,000 parts by weight of said ion exchanger based on 100 parts by weight of said medicinally active ingredient.

18. A solid preparation according to claim 2 which comprises 1 to 500 parts by weight of said ion exchanger based on 100 parts by weight of said powdery or granular preparation.

19. A solid preparation according to claim 2 wherein the contact of said medicinally active ingredient of the powdery or granular preparation with the powdery or granular ion exchanger is suppressed through a carrier or a coating composition.

20. A solid preparation according to claim 2 which comprises 2 to 200 parts by weight of a powdery or granular cation exchange resin having a mean particle diameter of 0.5 to 500 μm as said ion exchanger based on 100 parts by weight of said clad powdery or granular preparation having a mean particle diameter of 50 to 1,500 μm.

21. A solid preparation comprising a powdery or granular matrix-based or coated preparation containing a medicinally active ingredient having an unpleasant taste or odor, and a powdery or granular ion exchange resin, wherein the ion exchanger and the active ingredient are not in direct contact and the ratio of the mean particle diameter $D_p$ of said preparation to the mean particle diameter $D_i$ of said powdery or granular ion exchange resin is such that $D_p/D_i = 1/0.001$ to 0.8.

22. A solid preparation according to claim 21 which comprises 2 to 200 parts by weight of the powdery or granular cation exchange resin having a mean particle diameter of 1 to 100 μm based on 100 parts by weight of the matrix-based or coated preparation having a mean particle diameter of 100 to 1,500 μm, wherein the ratio of the mean particle diameter Dp of said preparation to the mean particle diameter Di of said powdery or granular cation exchange resin is such that Dp/Di=1/0.01 to 0.5.

23. A solid preparation according to claim 21 which comprises 3 to 180 parts by weight of the powdery or granular cation exchange resin based on 100 parts by weight of the matrix-based or coated preparation comprising a β-lactam antibiotic.

24. A solid preparation which comprises 5 to 150 parts by weight of a powdery or granular cation exchange resin based on 100 parts by weight of a granulated preparation having a basic group and comprising a β-lactam antibiotic having an unpleasant taste or odor which may be coated, wherein said powdery or granular cation exchange resin is attached or adhered to said granulated preparation and the contact of said resin with said medicinally active ingredient is suppressed through a carrier or a coating composition of said granulated preparation.

25. A solid preparation according to claim 24 which comprises the granulated preparation having a mean particle diameter of 100 to 1,500 μm which may be coated, and the powdery or granular cation exchange resin having a mean particle diameter of 1 to 100 μm, wherein the ratio of the mean particle diameter Dp of said granulated preparation to the mean particle diameter Di of said cation exchange resin is such that Dp/Di= 1/0.02 to 0.5.

26. A solid preparation according to claim 24 wherein said granulated preparation is a matrix-based preparation comprising 100 to 3,000 parts by weight of a carrier based on 100 parts by weight of said medicinally active ingredient, or a coated preparation coated with a coating composition in a proportion of 5 to 50% by weight based on the total weight.

27. A method of producing a solid preparation which comprises blending (A) a clad powdery or granular preparation of a medicinally active ingredient with (B) a powdery or granular ion exchanger, wherein the direct contact of the ion exchanger and the medicinally active ingredient is avoided or suppressed.

28. A method of producing a solid preparation according to claim 27, wherein the medicinally active ingredient has an unpleasant taste or odor.

29. A method of masking a taste or odor of a medicinally active ingredient which comprises allowing a powdery or granular preparation containing a medicinally active ingredient having a taste or odor to be co-existent with a powdery or granular ion exchanger, wherein the direct contact of the ion exchanger and the medicinally active ingredient is avoided or suppressed.

30. A method of masking a taste or odor of a medicinally active ingredient according to claim 29, wherein the medicinally active ingredient has an unpleasant taste or odor.

* * * * *